(12) United States Patent
Knifton et al.

(10) Patent No.: US 7,538,061 B2
(45) Date of Patent: May 26, 2009

(54) ONE-STEP PRODUCTION OF 1,3-PROPANEDIOL FROM ETHYLENE OXIDE AND SYNGAS WITH A COBALT-IRON CATALYST

(75) Inventors: John Frederick Knifton, Houston, TX (US); Talmadge Gail James, Conroe, TX (US); Lynn Henry Slaugh, Houston, TX (US); Paul Richard Weider, Houston, TX (US); Kevin Dale Allen, Prairieville, LA (US); Joseph Broun Powell, Houston, TX (US)

(73) Assignee: Shell Oil Company, Houston, TX (US)

( * ) Notice: Subject to any disclaimer, the term of this patent is extended or adjusted under 35 U.S.C. 154(b) by 1030 days.

(21) Appl. No.: 10/790,598

(22) Filed: Mar. 1, 2004

(65) Prior Publication Data
US 2004/0176648 A1 Sep. 9, 2004

Related U.S. Application Data

(62) Division of application No. 10/146,675, filed on May 15, 2002, now Pat. No. 6,750,373.

(60) Provisional application No. 60/291,827, filed on May 18, 2001.

(51) Int. Cl.
*B01J 31/12* (2006.01)
*B01J 31/20* (2006.01)
*B01J 31/22* (2006.01)
*B01J 31/24* (2006.01)
*B01J 31/18* (2006.01)

(52) U.S. Cl. ............ 502/162; 502/167; 502/174; 502/161; 568/867

(58) Field of Classification Search ............ 502/150
See application file for complete search history.

(56) References Cited

U.S. PATENT DOCUMENTS 3,456,017 A 7/1969 Smith et al. ............ 260/602

(Continued)

FOREIGN PATENT DOCUMENTS

JP 59138066 A * 8/1984

(Continued)

OTHER PUBLICATIONS

Gladfelter, W. et al., "Mixed Metal Clusters," Advances in Organometallic Chemistry v. 18, p. 207-273, Academic Press, 1980.*

(Continued)

*Primary Examiner*—Melvin C Mayes
*Assistant Examiner*—James Corno
(74) *Attorney, Agent, or Firm*—Richard B. Taylor

(57) ABSTRACT

Disclosed is a new catalyst composition comprising a bimetallic Co—Fe catalyst, optionally complexed with a ligand selected from a N-heterocycle, phosphine, or porphorine ligand, that provides a lower cost alternative for the one step synthesis of 1,3-propanediol (1,3-PDO) from ethylene oxide and synthesis gas. For example, a catalyst containing cobalt carbonyl: iron carbonyl with no ligand, or a catalyst containing a cobalt carbonyl: octaethylporphine iron acetate provide moderate yields of 1,3-PDO in a one step synthesis under mild conditions.

5 Claims, 4 Drawing Sheets

U.S. PATENT DOCUMENTS

| | | | |
|---|---|---|---|
| 3,463,819 A | 8/1969 | Smith et al. | 260/602 |
| 3,687,981 A | 8/1972 | Lawrence et al. | 260/340.7 |
| 3,917,737 A * | 11/1975 | Yoo | 585/277 |
| 4,238,357 A | 12/1980 | Pesa et al. | 252/431 N |
| 4,253,987 A | 3/1981 | Fiato | 252/429 R |
| 4,395,547 A | 7/1983 | Raghu et al. | 544/184 |
| 4,408,069 A | 10/1983 | Doyle | 560/232 |
| 4,433,177 A | 2/1984 | Lin et al. | 568/487 |
| 4,518,707 A * | 5/1985 | Soled et al. | 502/174 |
| 4,650,911 A | 3/1987 | Isogai et al. | 568/902 |
| 4,661,623 A * | 4/1987 | Chang et al. | 560/232 |
| 4,895,818 A | 1/1990 | Duggan et al. | 502/161 |
| 5,256,827 A | 10/1993 | Slaugh et al. | 568/454 |
| 5,304,686 A | 4/1994 | Slaugh et al. | 568/496 |
| 5,304,691 A | 4/1994 | Arhancet et al. | 568/867 |
| 5,344,993 A | 9/1994 | Slaugh et al. | 568/454 |
| 5,459,299 A | 10/1995 | Cheng | 219/267 |
| 5,463,144 A | 10/1995 | Powell et al. | 568/867 |
| 5,463,145 A | 10/1995 | Powell et al. | 568/867 |
| 5,463,146 A | 10/1995 | Slaugh et al. | 568/862 |
| 5,545,765 A | 8/1996 | Slaugh et al. | 568/454 |
| 5,545,766 A | 8/1996 | Powell et al. | 568/862 |
| 5,545,767 A | 8/1996 | Weider et al. | 568/867 |
| 5,563,302 A | 10/1996 | Weider et al. | 568/862 |
| 5,585,528 A | 12/1996 | Powell et al. | 568/862 |
| 5,672,778 A * | 9/1997 | Lyons et al. | 568/835 |
| 5,684,214 A | 11/1997 | Weider et al. | 568/862 |
| 5,689,016 A | 11/1997 | Weider et al. | 568/862 |
| 5,841,003 A | 11/1998 | Slaugh et al. | 568/867 |
| 6,245,707 B1 * | 6/2001 | Chu et al. | 502/167 |
| 6,436,280 B1 | 8/2002 | Harle et al. | 208/216 R |
| 6,468,940 B1 | 10/2002 | Knifton et al. | 502/162 |
| 6,469,222 B2 | 10/2002 | Knifton et al. | 568/867 |
| 6,545,190 B2 | 4/2003 | Allen et al. | 568/867 |
| 6,576,802 B2 | 6/2003 | Knifton et al. | 568/867 |
| 6,586,643 B2 | 7/2003 | Knifton et al. | 568/867 |
| 6,706,656 B2 | 3/2004 | Knifton et al. | 502/154 |
| 6,750,373 B2 | 6/2004 | Knifton et al. | 568/867 |
| 6,753,289 B2 | 6/2004 | Knifton et al. | 502/167 |
| 6,903,044 B2 | 6/2005 | Knifton et al. | 502/167 |

FOREIGN PATENT DOCUMENTS

| | | |
|---|---|---|
| WO | WO9418149 | 8/1994 |
| WO | 96/10552 | 4/1996 |
| WO | WO9610551 | 4/1996 |
| WO | 98/00471 | 1/1998 |
| WO | 98/42717 | 10/1998 |
| WO | 01/14299 A1 | 3/2001 |
| WO | 01/72675 A2 | 10/2001 |

OTHER PUBLICATIONS

J. Falbe, "Carbon Monoxide in Organic Synthesis," Springer-Verlag, NY (1970) Chapter 1, pp. 3-16.

Matsuzaka, H. et al., "Chemistry of Cobalt-Ruthenium Mixed Metal Clusters and Mixed Metal Complexes," retrieved from STN database Accession No. 1988:535737 XP002220900, Abstract, Structure, Nippon Kagaku Kaishi, No. 5, May 1988, pp. 705-713, XP002220899, ISSN: 0369-4577 Abstract, Figures 2, 7-9; Table 3.

* cited by examiner

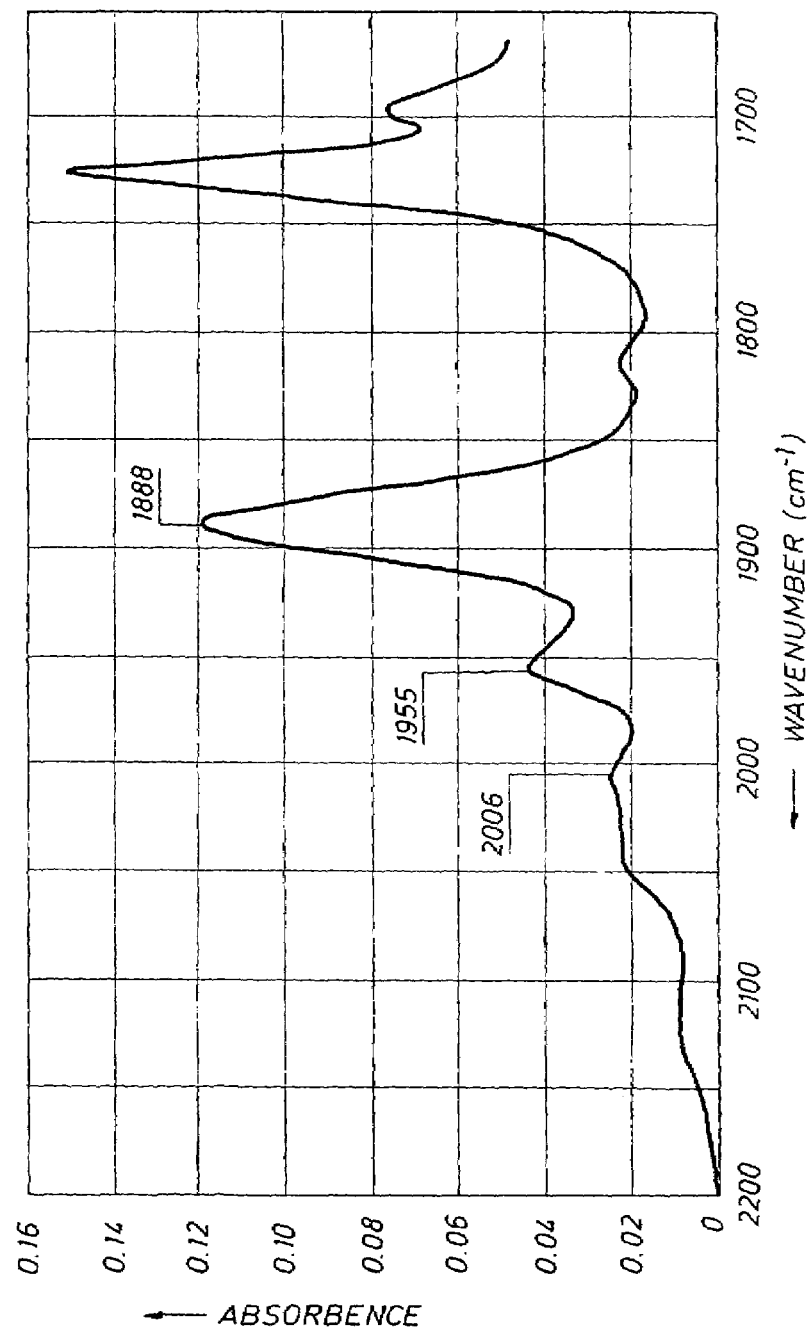

ONE-STEP PRODUCTION OF 1,3-PROPANEDIOL FROM ETHYLENE OXIDE AND SYNGAS WITH A COBALT-IRON CATALYST

This is a division of application Ser. No. 10/146,675 filed May 15, 2002, now U.S. Pat. No. 6,750,373, the entire disclosure of which is hereby incorporated by reference, which claims the benefit of U.S. Provisional Application No. 60/291,827 filed May 18, 2001,the entire disclosure of which is hereby incorporated by reference.

FIELD OF INVENTION

This invention relates to the synthesis of an aliphatic 1,3-diol, particularly 1,3-propanediol, from ethylene oxide and syngas in one step. More particularly this invention identifies a low cost bimetallic catalyst alternative that provides moderate yields under mild condition is in the one-step synthesis of 1,3-propanediol (1,3-PDO). The catalyst of the invention comprises a cobalt-iron catalyst, optionally in the presence of a ligand selected from N-heterocyclic, phosphine, or porphorine ligands, and optionally solubilized in an ether solvent.

BACKGROUND OF THE INVENTION

Aliphatic 1,3-diols, particularly 1,3-propanediol, have many applications as monomer units for polyester and polyurethane, and as starting materials for the synthesis of cyclic compounds. For example, CORTERRA® polymer is a polyester characterized by outstanding properties that is made of 1,3-propanediol (hereafter 1,3-PDO) and terephthalic acid. There is much interest in the art in finding new routes for synthesizing 1,3-PDO that are efficient, economical, and demonstrate process advantages.

U.S. Pat. Nos. 3,463,819 and 3,456,017 teach the hydroformylation of ethylene oxide to produce 1,3-propanediol and 3-hydroxypropanal (hereafter 3-HPA) using a tertiary phosphine-modified cobalt carbonyl catalyst.

U.S. Pat. No. 5,304,691, assigned to Shell, discloses a method of hydroformylating ethylene oxide to 3-hydroxypropanal and 1,3-propanediol in a single step using an improved catalyst system comprising a cobalt-tertiary phosphine ligand in combination with a ruthenium catalyst. In '691 1,3-PDO and 3-HPA are produced by intimately contacting an oxirane, particularly ethylene oxide (hereafter EO), a ditertiary phosphine-modified cobalt carbonyl catalyst, a ruthenium catalyst promoter, and syngas (carbon monoxide and hydrogen) in an inert reaction solvent at hydroformylation reaction conditions. A PDO yield of up to 86-87. mole % is reported, using a catalyst comprising cobalt ligated with 1,2-bis (9-phosphabicyclononyl)ethane as bidentate ligand, and either triruthenium(0) dodecacarbonyl or bis[ruthenium tricarbonyl dichloride] as cocatalyst.

The production of 1,3-PDO in one step with minimal impurities and byproducts involves recycle and requires a catalyst system with good stability both during 1,3-PDO synthesis and during product recovery and recycle. It would also be desirable if there were a low cost catalyst combination for the one-step synthesis of 1,3-PDO.

SUMMARY

In accordance with the foregoing, the present invention provides an alternative to the use of known hydroformylation catalyst compositions in the one-step synthesis of 1,3-PDO. The invention is a homogeneous catalyst system comprising:

a) A cobalt component comprising one or more preferably non-ligated cobalt compounds; and
b) An iron component, optionally ligated with a ligand selected from a N-heterocycle, phosphine, or porphorine moiety.

It has surprisingly been found the bimetallic cobalt-iron catalyst, optionally ligated, is effective in the one-step synthesis of 1,3-PDO and therefore offers the advantage of a lower cost alternative. For example, dicobalt octacarbonyl in combination with iron pentacarbonyl, with N,N-dimethyldodecylamine as promoter, solubilized in 1,3-dioxolane has been demonstrated to exhibit moderate yields with minimal precipitate formation in hydroformylation (synthesis gas pressure conditions).

The novel oxirane hydroformylation catalyst of the present invention involves a complex which is-postulated to be an cobalt: iron complex, alone, or optionally in combination with a ligand selected from a monodentate, bidentate or multidentate N-heterocyclic, a phosphine, or a porphorine. In this new bimetallic catalyst the ligand is believed to be predominantly attached to the iron rather than cobalt, as is the case in U.S. Pat. No. 5,304,691.

The invention also provides a one step process for preparing a 1,3-diol, comprising-the reaction of an oxirane with syngas at hydroformylation conditions in an inert solvent in the presence of the catalyst complex of this invention.

BRIEF DESCRIPTION OF THE DRAWINGS

FIG. 4 illustrates the IR spectrum of the cobalt-iron-porphorine catalyst during the one-step generation of 1,3-PDO.

DETAILED DESCRIPTION OF THE INVENTION

Figure 1:
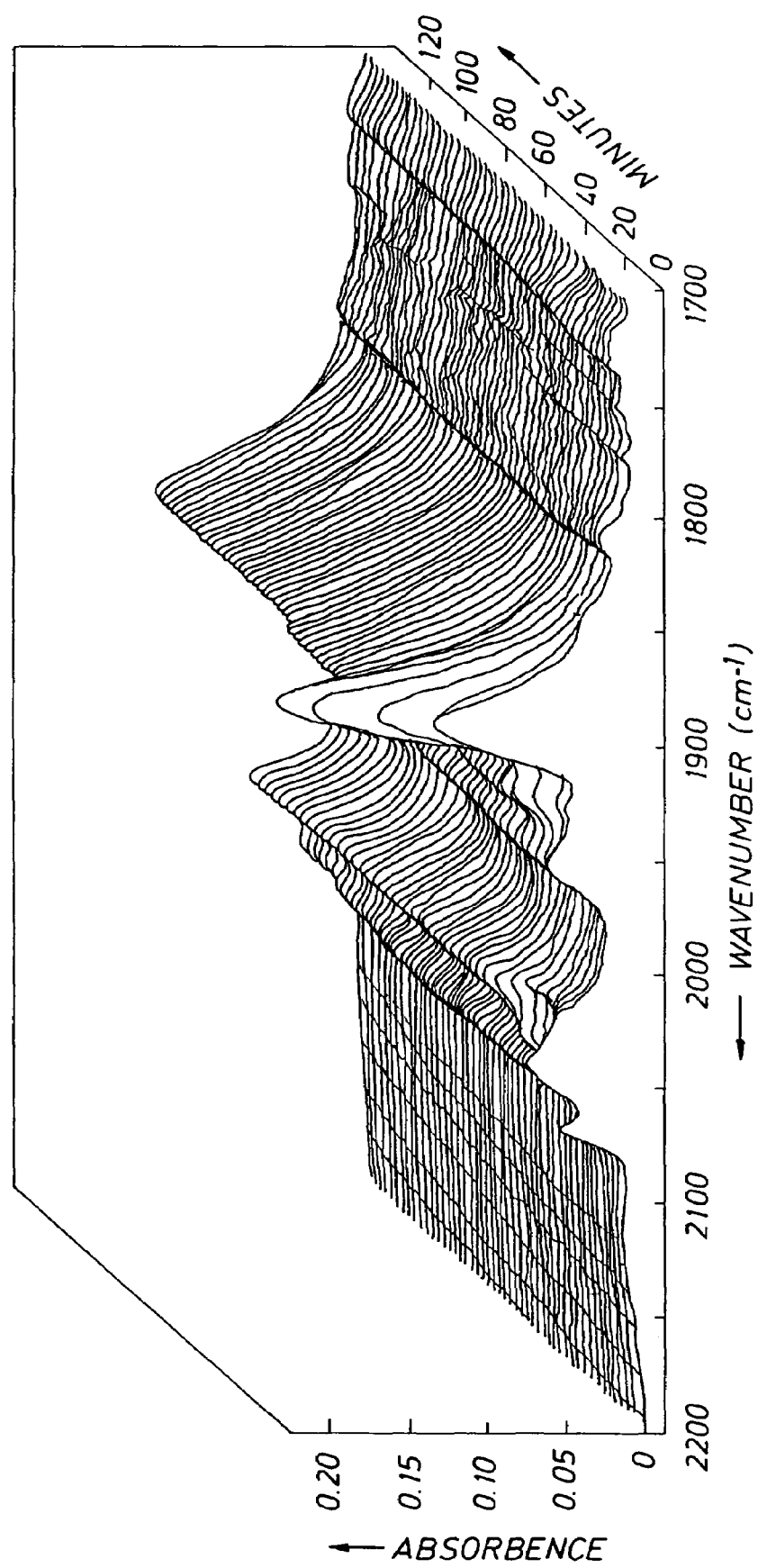
FIG. 1 is an IR cascade plot showing the formation of the cobalt-iron-porphorine catalyst as a function of time.

The selective hydroformylation/hydrogenation of ethylene oxide to 1,3-PDO in one step, represented by:

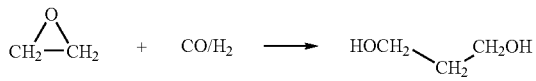

has been demonstrated using a bimetallic cobalt-iron homogeneous catalyst system, optionally in combination with soluble N-heterocycle, phosphine, or porphorine ligands, and optionally solubilized in an ether solvent.

The one-step process for synthesizing 1,3-PDO generally comprises intimately contacting ethylene oxide, carbon monoxide and hydrogen (syngas), and the bimetallic catalyst in a liquid-phase solution in an inert reaction solvent at a temperature of from about 30 to 150° C., and an elevated pressure.

Important aspects of the one-step process of the present invention include the use of hydrogen-rich synthesis gas, and operation at a somewhat higher pressure than used in '691, where the preferred operating pressure is closer to 1500 psi (10,340 kPa). In the present invention the preferred pressure for the one-step synthesis is preferably in the range of about 2000±250 psi (13,790±1725 kPa).

Other important factors in the development of this chemistry include efficient PDO recovery from the crude oxonated product solutions, and recycle of the active Co—Fe or Co—Fe-ligand catalyst.

In the present invention 1,3-diols are made by charging an oxirane, bimetallic catalyst alone, or optionally ligated and optionally solubilized in a non-reactive reaction solvent, and reaction solvent to a pressure reactor with the introduction of syngas (a mixture of hydrogen and carbon monoxide, suitably in a molar ratio of 1:1 to 8:1, preferably 2:1 to 6:1) under hydroformylation conditions. Also within the scope of the invention is the use of a promoter and/or cocatalyst.

The process-of-the-present invention may be carried out as a batch-type process, continuous process, or a mixture thereof.

In the operation of the present-invention combined, separate, or staged streams of EO, syngas and catalyst are charged to a reaction vessel, which can be a pressure reaction vessel such as a bubble column or a stirred autoclave, operated-batch-wise or in a continuous manner.

Oxiranes of up to 10 carbon atoms, preferably up to 6 carbon atoms, and ethylene oxide, in particular, may be converted into their corresponding 1,3-diols by the hydroformylation reaction with syngas in the presence of the catalyst complex of the present invention.

An essential part of the present invention is the use of the Co—Fe or Co—Fe-ligand complex. The combination of the present invention is believed to comprise a novel class of modified bimetallic catalysts. The characterizing feature of this novel class involves an oxidized iron metal that is optionally ligated to a ligand selected from a monodentate, bidentate, or multidentate N-heterocycle, a phosphine, or porphorine ligand, with a cobalt compound as the counter ion.

Suitable iron compounds include, but are not limited to iron carbonyls as well as iron salts that are readily reduced to the zero valence state by heat treatment in an atmosphere of hydrogen and carbon monoxide. Examples of such iron salts include iron carboxylates such as acetates, octanoates, stearates, etc., as well as iron salts of mineral acids such as phosphates, chlorides, fluorides, sulfates, sulfonates, etc. Operable also are mixtures of these iron salts. A further possibility is the use of organometallic iron compounds, wherein the iron is bonded to one or more organic fragments, such as the cyclopentadiene, pentamethylcyclopentadiene, or cyclooctatetraene cyclic structures. Suitable examples include bis(cyclopentadienyl)iron, commonly known as ferrocene, as well as derivatives thereof. The reduction of said salts or organometallic compounds may be performed prior to their use as catalysts, or it may be accomplished simultaneously with the hydroformylation process. The examples demonstrate the particular usefulness of iron carbonyls, including iron pentacarbonyl, Fe $(CO)_5$, diiron nonacarbonyl. $Fe_2(CO)_9$, and triiron dodecarbonyl, $Fe_3(CO)_{12}$.

As noted, suitable ligands are selected from N-heterocycles, including monodentate, bidentate, and multidentate N-heterocycles, phosphine, and porphorine ligands.

A large number of N-heterocyclic compounds have been identified as suitable ligands for the one step PDO synthesis using the cobalt-iron catalyst couple. Suitable types of monodentate, bidentate, and multidentate N-heterocyclic ligands include, but are not limited to: Diazines such as pyrimidine, pyrazine, pyridazine, as well as benzodiazines such as quinazoline and quinoxaline; bispyridines such as 2,2'-dipyridyl (DIPY), 2,2'-bipyrimidine (BPYM), 1,10-phenanthroline (PHEN), di-2-pyridyl ketone, 4,4'-dimethyl-2,2'-dipyridyl, 5,6-dimethylphenanthroline, 4,7-dimethylphenanthroline, 2,2'-biquinoline, neocuproine, and 2,2'-dipyridylamine; multipyridines such as 2,4,6-tripyridyl-s-triazine(TPTZ), 3,6-di-2-pyridyl-1,2,4,5-tetrazine, 2,2':6',2"-terpyridine, 2,3-bis(pyridyl)pyrazine, and 3-(2-pyridyl)-5,6-diphenyl-1,2,4-triazine; pyridine, 3-hydroxypyridine, and quinoline, particularly the lower cost homologues derived from coal-tar extracts; as well as certain 2,6-pyridyl-diimines, such as 2,6-bis(N-phenyl, methylimino)pyridine (BPMIP) and 2,6-bis[N-(2,6-diisopropylphenyl)methylimino]pyridine (BDPMIP). Aliphatic diimines-may also be employed as ligands in the present invention. Here suitable aliphatic diimine ligands include N,N-di-tert-butyldiazobutadiene (DTBDB).

Suitable phosphine ligands for use in this complex include, but are not limited to, tertiary diphosphines of the general formula:

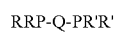

wherein each group R and R' independently or jointly is a hydrocarbon moiety of up to 30 carbon atoms, and Q is an organic bridging group of 2 to 4 atoms in length. The group R or R', when monovalent, may be alkyl, cycloalkyl, bicycloalkyl or aryl, and preferably of up to 20 carbon atoms, more preferably of up to 12 carbon atoms. Alkyl and/or cycloalkyl groups are preferred. The group Q is preferably composed of carbon atoms, which may form part of a ring system such as a benzene ring or a cyclohexane ring. More preferably Q is an alkylene group of 2, 3 or 4 carbon atoms in length, most preferably of 2 carbon atoms in length. A non-limiting list of illustrative diphosphines of this class include:

1,2-bis(dimethylphosphino)ethane; 1,2-bis(diethylphosphino)ethane; 1,2-bis(diisobutylphosphino)ethane; 1,2-bis(dicyclohexylphosphino)ethane; 1,2-bis(2,4,4-trimethylpentylphosphino)ethane; 1,2-bis(diethylphosphino)propane; 1,3-bis(diethylphosphino)propane; 1-(diethylphosphino)-3-(dibutylphdsphino)propane; 1,2-bis(diphenylphosphino)ethane; 1,2-bis(dicyclo-hexylphosphino)ethane; 1,2-bis-(2-pyridyl, phenylphosphanyl)benzene; 1,2-bis(dicyclo-pentylphosphino)ethane; 1,3-bis(2,4,4-trimethyl-pentylphosphino)propane; 1,2-bis(diphenylphosphino)benzene, and the like. These groups R and R' may be substituted with non-hydrocarbon groups themselves. Both groups R and/or both groups R' may also form a ring with the phosphorus atom(s), such as a phosphacycloalkane of from 5 to 8 atoms. Examples of 5-ring systems (phospholano-based ligands) include 1,2-bis(phospholano)ethane, 1,2-bis(2,5-dimethylphospholano)benzene, optically pure (R,R), (R,S), (S,S) 1,2-bis(2,5-dimethylphospholano)ethane or its racemic mixture, and the like. The ring itself may be part of a multi-ring system. Examples of such ring systems may be found in the aforementioned '691 patent and in WO-A-9842717 (both herewith incorporated by reference in the entirety). In the former, phosphabicyclononyl groups are described and in the latter, adamantyl-like groups and phosphatrioxa-tricyclodecyl groups in particular are described. Diphosphines, wherein both groups R and R' form a ring with the phosphorus atom, are preferred. Examples include 1,2-bis(9-phosphabicyclononyl)ethane (B9PBN).

Ditertiary phosphine ligands are commercially available. Catalysts prepared therefrom are known in the art and their method of preparation is described in detail in U.S. Pat. Nos. 3,401,204 and 3,527,818, which are both incorporated by reference herein in the entirety. The phosphine ligands may also be partially oxidized to phosphine oxides in the manner described in the '691 patent.

Porphorine ligands generally comprise four pyrrole-type ring moieties, arranged in a cyclic structure, that may optionally also incorporate various alkyl and aryl substituents both on the pyrrole rings and on the connecting methine groups. Suitable porphorine ligands in the practice of this invention include octaethylporphorines and tetraphenyporphorines, as well as the closely related phthalocyanines. Example 2, infra, demonstrates the use of 2,3,7,8,12,13,17,18-octaethyl-21H, 23H-porphine iron (III) acetate (OEPFeAc) as the iron source for 1,3-PDO synthesis.

The molar ratio of N- or P-ligand to iron atom may vary from 4:1 to 1:4, but preferably from 2:1 to 1:2, and in many cases, it is most preferably about 1:1.

Suitable cobalt sources include salts that are reduced to the zero valence state by heat-treatment in an atmosphere of hydrogen and carbon monoxide. Examples of such salts comprise, for instance, cobalt carboxylates such as acetates, octanoates, etc., which are preferred, as well as cobalt salts of mineral acids such as chlorides, fluorides, sulfates, sulfonates, etc. Operable also are mixtures of these cobalt salts. It is preferred, however, that when mixtures are used, at least one component of the mixture be a cobalt alkanoate of 6 to 12 carbon atoms. The reduction may be performed prior to the use of the catalysts, or it may be accomplished simultaneously with the hydroformylation process in the hydroformylation zone.

The counter ion, for best results, is believed to be the cobalt tetracarbonyl anion, ($[Co(CO)_4]^-$), having a characteristic cobalt carbonyl IR band in the region 1875 to 1900 $cm^{-1}$, particularly in the region 1888 $cm^{-1}$. However, this ion in the active catalyst can be a modification thereof. Part of the cobalt compound may be modified with one of the ligands specified herein, e.g., up to 75 mole % excess, say up to 50 mole % or less. However, the counter ion is preferably the non-ligated cobalt tetracarbonyl anion mentioned before. Cobalt carbonyls can be generated by reaction of a starting cobalt source such as cobalt hydroxide with syngas, as described in J. Falbe, "Carbon Monoxide in Organic Synthesis", Springer-Verlag, NY (1970), or otherwise.

The oxidation state of the iron atom during the 1,3-PDO synthesis can vary substantially (in theory, iron may have a valence of at least from zero to four), and this oxidation state may well change during the course of the hydroformylation reaction. Accordingly, the molar ratio of iron to cobalt may vary within relatively broad ranges. Sufficient cobalt (0) should be added to completely oxidize all of the complexed-iron employed. An excess of cobalt can be added, but is not of particular value. Suitably, the iron:cobalt molar ratio varies from 4:1 to 1:4, preferably from 2:1 to 1:3, more preferably from 1:1 to 1:2.

The initial molar stoichiometry ratio of cobalt to iron: ligand is suitably at least in the range of 0.5 to 4 moles cobalt: 0.1 to 2 moles iron: 0 to 2 moles N-ligand. A preferred range would be about 1 to 3 moles cobalt to 3.2 to 1.5 moles iron to 0 to 1 moles ligand. One formulation, (See Example 2), was cobalt:iron:OEPFeAc ligand in molar stoichiometry of about 1:0.35:0.35, respectively.

In the present invention, the preferred method of preparing the cobalt-iron or cobalt-iron-ligand catalyst is the self-assembly method, wherein all catalyst components are brought together at the same time. As demonstrated in Examples 1-4, the cobalt-iron-ligand complexes may be generated by self-assembly, in one step, when solubilized in a suitable ether solvent under synthesis-gas conditions. The conditions and, in particular, the solvent, are selected such as to favor the formation of a ligated iron species, rather than a ligated cobalt species. The presence of the Fe-ligated species rather than the Co-ligand species may be confirmed by e.g. IR analysis.

Also within the scope of the invention is the stepwise preparation of the catalyst, as follows: The first step in the catalyst preparation is synthesis of the Fe-ligand complex. This may be done by bringing a suitable iron source, e.g., iron pentacarbonyl in contact with the selected ligand. Alternatively, other readily available iron carbonyl derivatives, such as iron nonacarbonyl or iron dodecarbonyl may be employed instead of iron pentacarbonyl. Further alternatives include the use of sources that, under a syngas atmosphere, will in-situ form iron carbonyl species. These less expensive iron sources may include iron (III) nitrate and iron (III) stearate, and iron(III) sulfate. The iron-N-heterocyclic, phosphine, or porphorine ligand complex may for instance be made by reacting iron pentacarbonyl with a stoichiometric amount of a selected ligand in a solvent at a temperature within the range of 25 to 150° C., suitably 100 to 110° C., under a carbon monoxide or synthesis gas atmosphere, for a 1 to 24 hours (i.e. until completion). At this point, optionally, said iron-ligand complex may be isolated as a discrete material.

Next, in the stepwise method, the Fe-ligand complex is brought into contact with a suitable cobalt carbonyl compound by means of a redox reaction to form the Fe—Co-ligand complex, again at the aforementioned (noncritical) conditions. A suitable cobalt source is dicobalt octacarbonyl, but other cobalt complexes and salts may be used as well. For instance, the selected cobalt carbonyl, and optional promoters, if any, are added to the solution which is then maintained at the elevated temperature (from 25 to 150° C.) for a time of about 15 minutes to 24 hours. Again, optionally, the new cobalt-iron-ligand complex may be isolated and characterized.

Typically, whether said active Co—Fe or Co—Fe-ligand catalyst is generated by self assembly, or step-wise, it exhibits characteristic IR bands-in the metal-carbonyl region, particularly a strong cobalt carbonyl band in the region 1875 to 1900 $cm^{-1}$ due to the $[Co(CO)_4]^-$ anion, plus a series of iron-carbonyl bands in the 1950 to 2050 $cm^{-1}$ region that are postulated to be due to cationic iron carbonyl species.

The conditions at which these compounds are allowed to form a complex are not critical. Temperature and pressure may vary within the ranges given below with respect to the hydroformylation reaction, for example 25 to 150° C. Syngas may be used as gas cap during the complex formation. It is preferable to use a solvent, preferably the solvent used in the hydroformylation reaction. Obviously, this solvent should be capable of dissolving the active catalyst, without affecting its properties. Suitable solvents include the ethers described below for use in the hydroformylation process, in particular cyclic aliphatic ethers.

The optimum ratio of oxirane in the feed to Co—Fe or Co—Fe-ligand complex will in part depend upon the particular complex employed. However, molar ratios of oxirane to the cobalt within the Co—Fe-ligand complex from 2:1 to 10,000:1 are generally satisfactory, with molar ratios of from 50:1 to 500:1 being preferred.

The reaction solvent should be inert, meaning that it is not consumed during the course of the reaction. Ideal solvents for the invention process will solubilize the feed and products during the course of the reaction, but allow phase separation at reduced temperatures. Suitable solvents are described in U.S. Pat. No. 5,304,691 incorporated herein by reference in the entirety. Good results may be achieved with ethers, particularly cyclic, aliphatic ethers, optionally in combination with an alcohol, such as ethanol or tert-butanol, and/or an aromatic hydrocarbon, such as toluene and the chlorobenzenes.

Promoters may be employed. Suitable promoters are described in U.S. Pat. No. 5,304,691, previously cited. Examples of promoters that work well, are readily available, and have demonstrated the promotion of EO conversion are tertiary amines such as N,N-dimethyldodecylamine and triethylamine, as well as alkali salts such as sodium acetate.

For best results, the one step hydroformylation/hydrogenation is conducted under conditions of elevated temperature and pressure. Reaction temperatures range from 30 to 150° C., preferably from 50 to 125° C., and most preferably from 60 to 110° C.

The reaction pressure (total pressure, or partial pressure if inert gaseous diluents are used) should be at least 100 psi (690 kPa). A suitable operating pressure is in the range of 100 psi (690 kPa) to 4000 psi (27,580 kPa), preferably from 1500 psi to 2500 psi (10,340 to 17,240 kPa), and most preferably about 2000 psi±250 psi (13,790±1725 kPa). In a batch process, the reaction will generally be complete within 1 to 5 hours.

The components of the feed streams are contacted in a suitable reaction solvent in the presence of the catalyst complex of the present invention. The EO will preferably be maintained throughout the reaction in a concentration not less than about 0.2% by weight, generally within the range of 0.2 to 20% by weight, preferably 1 to 10% by weight, based on the total weight of the reaction mixture. The process of the invention can be carried out in a continuous-mode, while maintaining said EO concentration, by for instance, staged EO addition.

At the conclusion of the hydroformylation reaction, the 1,3-PDO is recovered from the product mixture by conventional methods such as selective extraction, fractional distillation, phase separation, selective crystallization, and the like. The unreacted starting materials as well as the catalyst and reaction solvent may, and preferably are, recycled for further use.

Partitioning of the reaction mixture can be promoted by the addition of a phase-split inducing agent. Suitable agents include glycols such as ethylene glycol and linear alkanes such as dodecane. Such an agent will be added to the reaction mixture in an amount within the range of about 2 to 10% by weight, preferably 4 to 8% by weight, based on the total reaction mixture. Alternate methods include addition of 1,3-propanediol into the reaction mixture to bring product concentration up to the target proportion. Also, miscibilizing alcohols and agents with similar polarity such as ethanol, propanol and isopropanol can be added initially, then removed prior to the subsequent inducement of the phase separation.

Commercial operation will require efficient catalyst recovery with multiple cycles of essentially complete recycle of catalyst to the reaction. The preferred catalyst recovery process involves separation of the two liquid phase mixture noted previously and recycle of the bulk solvent phase to the reactor and return therewith of at least 60 to 90% by weight of the starting catalyst.

In a preferred manner of running the process, reaction conditions such as oxirane concentration, catalyst concentration, solvent, product concentration, reaction temperature and the like are selected so as to achieve a homogeneous reaction mixture at elevated temperatures and cause a partitioning of the reaction mixture into an upper solvent phase containing much of the catalyst and a lower phase containing most of the 1,3-propanediol upon cooling the mixture. Such a partitioning facilitates isolation and recovery of product, recycle of catalyst and removal of heavy ends from the solvent system. This process is referred to as a phase separation catalyst recycle/product recovery method.

In this process, the reactor contents are allowed to settle or are transferred to a suitable vessel at pressures ranging from atmospheric to near reaction pressure where, upon-slight or considerable cooling, distinct phases may form that are substantially different, being considerably rich in 1,3-propanediol product, or in catalyst and solvent. The phase rich in cobalt-iron catalyst and solvent is directly recycled for further reaction with feed materials. Product 1,3-PDO is recovered from the product rich phase by conventional methods.

Formulations containing cobalt carbonyls in combination with iron carbonyls, iron porphines, and iron phosphines provided one-step synthesis of 1,3-PDO when solubilized in suitable ether solvents. The cobalt carbonyl-iron carbonyl combinations are particularly effective (See Example 1).

The following examples will serve to illustrate the invention disclosed herein. The examples are intended only as a means of illustration and should not be construed as limiting the scope of the invention in any way. Those skilled in the art will recognize many variations that may be made without departing from the spirit of the disclosed invention.

EXAMPLE 1

To a 100 ml stirred Parr autoclave, equipped with the necessary temperature and pressure controls, was charged 23 ml of dry, nitrogen-flushed, 1,3-dioxolane, 113 mg of dicobalt octacarbonyl (0.66 mmole Co), 125 mg of iron pentacarbonyl (0.64 mmole), and 90 mg of N,N'-dimethyldodecylamine. The autoclave was sealed and pressured to 1300 psi (8,960 kPa) with 1:4 ($CO:H_2$) synthesis gas, and heated to 90° C. for three hours, with stirring, at 1500 psi (10,340 kPa). At this point, the reactor and contents were cooled to 5° C. and the gases vented. Ethylene oxide (EO, 3.9 gm, 89 mmole) was added to the reactor system and, after repressuring to 1800 psi (12,410 kPa) with ¼ syngas, the-reactor was heated to 90° C., for 2 hours, at 2000 psi (13,790 kPa) total pressure. Additional synthesis gas was supplied as needed.

After cooling again to 5° C., and venting, 27.8 gm of a single-phase, clear, orange-brown, liquid product, with no apparent particulate component, was recovered and analyzed by GC-ms/IR. 1,3-Propanediol was confirmed to be present; the concentration of 1,3-PDO in the crude product effluent was 1.5%, the estimated yield of 1,3-PDO was determined to be 5.6 mole %, basis the EO charged. The primary co-products were 3-hydroxypropanal (4.8% conc. ), acrolein (1.5% conc. ), and acetaldehyde (1.1% conc. ).

EXAMPLE 2

Following the procedures of Example 1, the 100 ml Parr reactor was charged with 23 ml of 1,3-dioxolane, 113 mg of dicobalt octacarbonyl (0.66 mmole Co), 152 mg of 2,3,7,8, 12,13,17,18-octaethyl-21H,23H-porphine iron (III) acetate (0.23 mmole), and 90 mg of N,N-dimethyldodecylamine promoter. After pretreatment with synthesis gas at 90° C., followed by EO addition (3.5 gm) and hydroformylation again at 90° C., under 2000 psi (13,790 kPa) of ¼ ($CO:H_2$) synthesis gas for 2 hours, 29. 1 gm of dark red liquid product was recovered with no sign of precipitates. Analyses by gc and gc-ms/ir confirmed the presence of 1,3-PDO. The concentration of 1,3-PDO in the crude product effluent-was 1.1%, estimated 1,3-PDO yield was 5.1 mole %, basis the EO charged.

EXAMPLE 3

Following the procedures of Example 1, a 50 ml capacity reactor fitted with in-situ infrared (IR) capability was charged with 23 ml of 1,3-dioxolane, 116 mg of dicobalt octacarbonyl (0.68 mmole Co), 149 mg of 2,3,7,8,12,13,17,18,-octaethyl-21H,23H-porphine iron(III) acetate (0.22 mmole), and 89 mg of N,N-dimethyldodecylamine. The cobalt-iron-porphorine solution was then pretreated with synthesis gas (1000 psi; 6900 kPa; ¼ CO:$H_2$) at 90° C. Following the addition of EO (2.0 gm), hydroformylation was conducted at 90° C. under 1500 psi (10,340 kPa) of ¼, CO/$H_2$ syngas.

Figure 2:
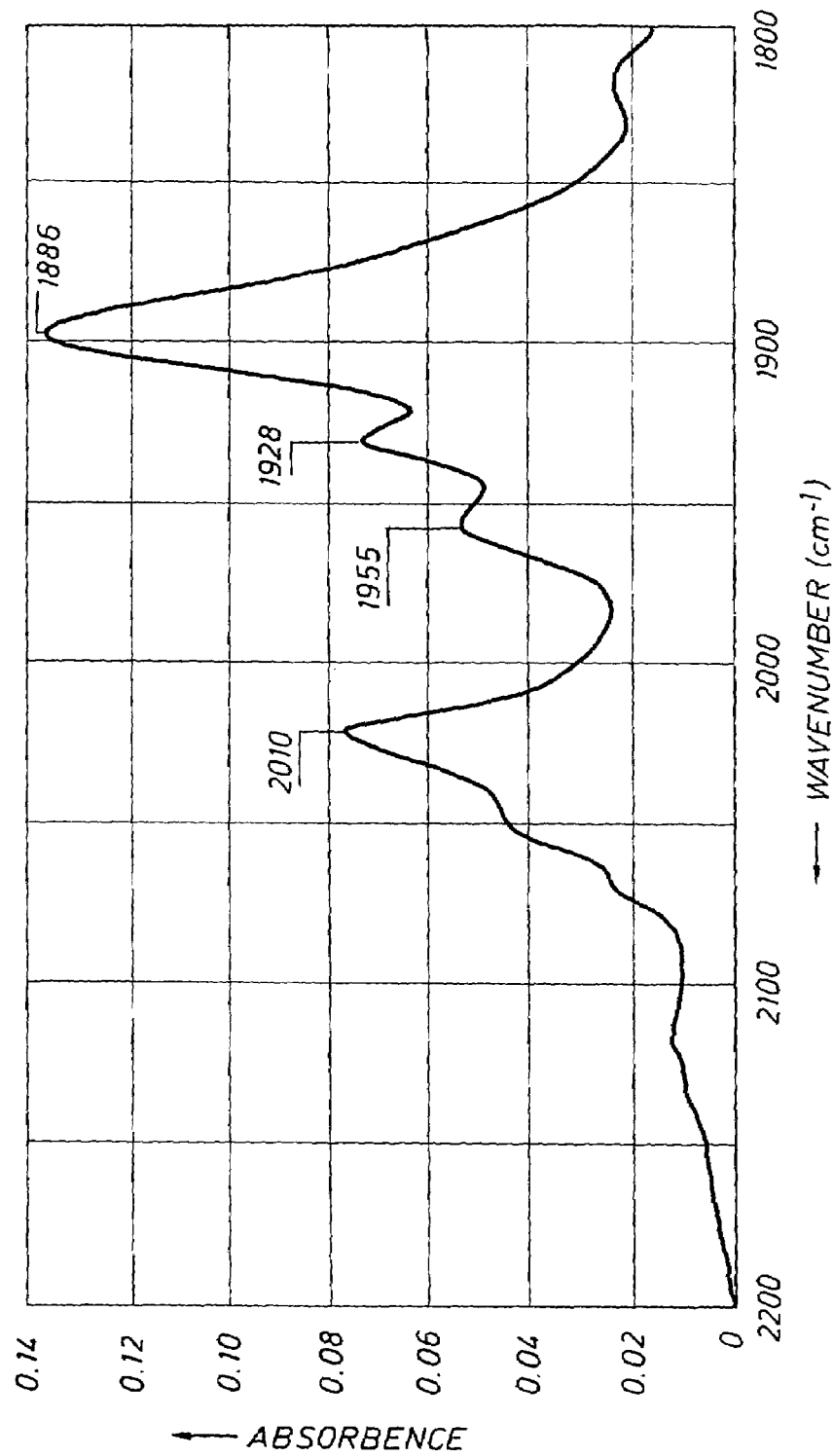
FIG. 2 is the IR spectrum of the cobalt-iron-porphorine catalyst after preforming in 1,3-dioxolane.
Figure 3:
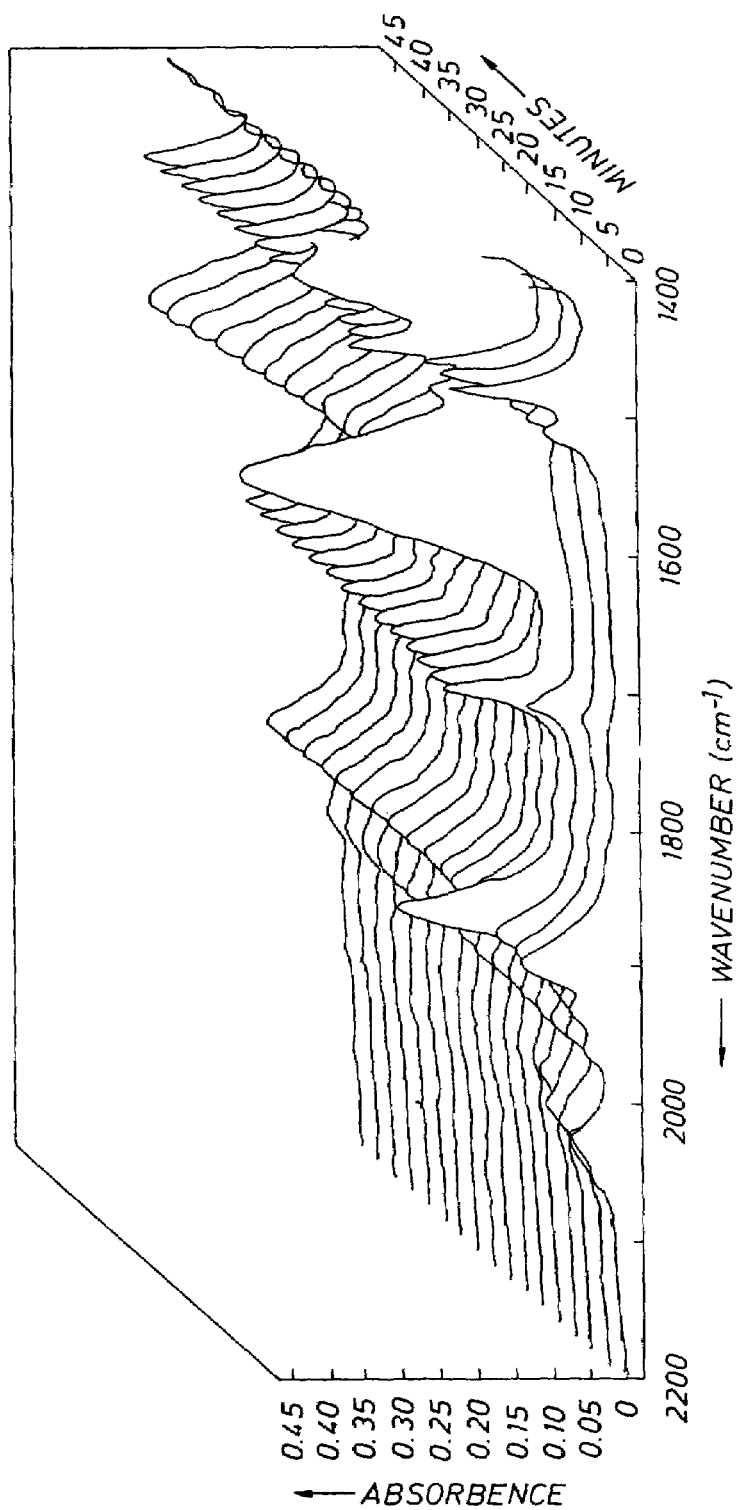
FIG. 3 is an IR cascade plot showing the cobalt-iron-porphorine catalyst during the one-step conversion of ethylene oxide and synthesis gas to 1,3-propanediol.

Typical IR spectra of the cobalt-iron-porphorine solution during, and after completion, of the pretreatment step, showing the characteristic bands in the metal-carbonyl region due to cobalt carbonyl species (1886 cm$^{-1}$) and iron carbonyls (1955 and 2010 cm$^{-1}$) are illustrated in FIGS. 1 and 2. The spectra of the reacting solutions after EO addition are illustrated in FIGS. 3 and 4. The final product solution was clear, with no signs of precipitates.

EXAMPLE 4

In Example 4 which generally followed the procedures of Example 1, the bimetallic catalyst comprised dicobalt octacarbonyl and 2,3,7,8,12,13,17,18,-octaethyl-21H,23H-porphine iron (III) acetate (Co:Fe atomic ratio 1:0.3), but the solvent was a mix of chlorobenzene and toluene (1:1 by volume). The catalyst was pretreated at 90° C. under 1500 psi (10,340 kPa) of synthesis gas (1:4, CO/$H_2$) for 3 hours. After cooling, depressuring, and EO addition, the hydroformylation reaction was run at 2000 psi (13,790 kPa) with ¼ (CO/$H_2$) gas. The EO uptake time was 1¼ hr. The product phase weighed 23.7 gms. 1,3-PDO was confirmed to be present, and the estimated yield of 1,3-PDO was determined to be 4.4 mole %.

EXAMPLES 5 TO 23

In Examples 5 to 23 the procedures followed were as described in Example 1, employing various combinations of cobalt and iron compounds, alone, or complexed with a variety of ligands selected from N-heterocyclic, phosphine, and porphorine ligands. For example, in runs 5-7, shown in Table 1, the bimetallic catalyst composition incorporated 2,3,7,8,12,13,17,18-octaethyl-21H,23H-porphorine iron (III)acetate has been examined using different initial Co:Fe ratios. The presence of 1,3-PDO in the product was confirmed.

TABLE 1

| EXP. | Catalyst | Solvent | Temp ° C. | Time EO Uptake (hrs) | Product Phases | wt(g) | Conc. (%) PDO | HPA | PDO Production (mmole) | PDO Yield (mole %) |
|---|---|---|---|---|---|---|---|---|---|---|
| 5 | Co-½ OEPFeAc | 1,3-dioxolane | 90$^a$ | 3 | P | 20.8 | N.D. N.D. | 3.1 0.8 | N.D. N.D. | <0.1 |
| 6 | Co- OEPFeAc | " | 90$^a$ | >2.5 | P | 19.2 | 0.01 N.D. | 0.2 N.D. | <0.1 N.D. N.D. | <0.1 |
| 7 | Co-⅓ OEPFeAc | " | 90$^a$ | 3.25 | P | 20.3 | 0.04 N.D. | 2.7 0.8 | <0.1 0.1 N.D. 0.1 | 0.2 |

$^a$Run in 50 cc Parr reactor at 2000 psi (13,790 kPa) with ¼ (CO/H2) gas

Additional runs were carried out using as ligands N,N-di-tert-butyldiazobutadiene (DTBDB), 2,6-bis(N-phenyl,methylimino)pyridine (BPMIP), 1,2-bis(9-phosphabicyclononyl)ethane (B9PBN), and 1,2-bis(diethylphosphino)ethane (BDEPE); experimental data are noted in Table 2. The presence of 1,3-PDO was confirmed in each example.

TABLE 2

| EXP. | Catalyst | Solvent | Temp ° C. | Time EO Uptake (hrs) | Product Phases | wt(g) | Conc. (%) PDO | HPA | PDO Production (mmole) | PDO Yield (mole %) |
|---|---|---|---|---|---|---|---|---|---|---|
| 8 | Co$_2$(CO)$_8$— Fe(CO)$_5$ DTBDB | 1,3-dioxolane | 90$^a$ | 1.75 | P | 26.0 | 0.1 N.D. | 0.5 N.D. | 0.3 N.D. | 0.3 |
| 9 | Co$_2$(CO)$_8$— Fe(CO)$_5$ BPMIP | " | 90$^a$ | 2 | P | 27.7 | N.D. N.D. | N.D. N.D. | 0.3 N.D. N.D. N.D. | <0.1 |

TABLE 2-continued

| EXP. | Catalyst | Solvent | Temp °C. | Time EO Uptake (hrs) | Product Phases | wt(g) | Conc. (%) PDO | HPA | PDO Production (mmole) | PDO Yield (mole %) |
|---|---|---|---|---|---|---|---|---|---|---|
| 10 | Co$_2$(CO)$_8$—Fe(CO)$_5$ B9PBN[b] | " | 90[a] | <1 | P | 27.5 | 0.1 N.D. | 1.3 N.D. | 0.4 N.D. 0.3 | 0.5 |
| 11 | Co$_2$(CO)$_8$—Ru(CO)$_{12}$ BDEPE[b] | " | 90[b] | <1 | P | 27.5 | N.D. N.D. | 0.5 N.D. | N.D. N.D. N.D. | <0.1 |

[a] Run at 2000 psi (13,790 kPa) with ¼ (CO/H2) gas
[b] Co—Fe-ligand pretreated at 130° C.

The N-heterocyclic ligand, 2,2'-dipyridyl (DIPY) was employed in Examples 13, 14, 17, 19, 20, 21, and 23; the diimine, 2,6-bis(N-phenyl, methylimino)pyridine (BPMIP) in Examples 15 and 16, and 2,4,6-tripyridyl-s-triazine (TPTZ) was used in 18, as noted-in Tables 3 and 4. Ferrocene was the iron source in Example 12, and iron (II) phthalocyanine in Example 22. The presence of 1,3-PDO was confirmed.

Combinations of cobalt-ruthenium-iron carbonyls with 2,2'-dipyridyl, in 1,3-dioxolane solvent, were employed as catalysts in Examples 20 and 21. The estimated yields of 1,3-PDO in each of these two examples was ca. 55 mole %, basis EO charged.

TABLE 3

| EXP. | Catalyst | Solvent | Temp °C. | Time EO Uptake (hrs) | Product Phases | wt(g) | Conc. (%) PDO | HPA | PDO Production (mmole) | PDO Yield (mole %) |
|---|---|---|---|---|---|---|---|---|---|---|
| 12 | Co$_2$(CO)$_8$(C$_5$H$_5$)$_2$Fe | 1,3-dioxolane | 90[a] | 2 | P | 29.2 | N.D. N.D. | 2.8 0.3 | N.D. N.D. | <0.1 |
| 13 | Co$_2$(CO)$_8$—Fe(CO)$_5$ DIPY[b] | " | 120[a] | 3 | P | 28.4 | 0.2 N.D. | 0.3 N.D. | <0.1 0.6 N.D. | 0.6 |
| 14 | Co$_2$(CO)$_8$—Fe(NO$_3$)$_3$ DIPY[a] | " | 90[a] | 3 | P | 26.8 | N.D. N.D. | N.D. N.D. | 0.6 N.D. N.D. | <0.1 |
| 15 | Co$_2$(CO)$_8$—Fe(CO)$_5$— BPMIP[a] | ClC$_6$H$_5$/ C$_7$H$_8$ | 90[a] | 3 | P | 24.9 | 0.02 0.3 | 0.2 1.5 | <0.1 0.2 0.3 | 0.6 |
| 16 | Co$_2$(CO)$_8$—Fe(CO)$_5$— BPMIP[a] | 1,3-dioxolane | 90[a] | 1 | P | 25.9 | 0.4 N.D. | 3.8 0.9 | 0.5 1.3 N.D. 1.3 | 1.6 |

[a] Run at 2000 psi (13,790 kPa) with ¼ (CO/H2) gas
[b] Co—Fe-ligand pretreated at 150° C.

TABLE 4

| EXP. | Catalyst | Solvent | Temp °C. | Time EO Uptake (hrs) | Product Phases | wt(g) | Conc. (%) PDO | HPA | PDO Production (mmole) | PDO Sel. (%) | PDO Yield (mole %) |
|---|---|---|---|---|---|---|---|---|---|---|---|
| 17 | Co$_2$(CO)$_8$—Fe(CO)$_5$ DIPY | 1,3-dioxolane | 90[a] | 2.25 | P | 26.8 | N.D. N.D. | 0.6 N.D. | N.D. N.D. <0.1 | N.D. | <0.1 |

TABLE 4-continued

| EXP. | Catalyst | Solvent | Temp °C. | Time EO Uptake (hrs) | Phases | Product wt(g) | Conc. (%) PDO | Conc. (%) HPA | PDO Production (mmole) | PDO Sel. (%) | PDO Yield (mole %) |
|---|---|---|---|---|---|---|---|---|---|---|---|
| 18 | $Co_2(CO)_8$—$Fe(CO)_5$ TPTZ[a] | " | 90[a] | 2.25 | P | 27.6 | 0.02 N.D. | 0.5 N.D. | <0.1 <0.1 N.D. | N.D. | <0.1 |
| 19 | $Co_2(CO)_8$—$Fe(NO_3)_3$ DIPY[b] | " | 90[a] | 3 | P | 26.7 | 0.08 N.D. | 0.9 N.D. | <0.1 <0.1 N.D. | N.D. | <0.1 |
| 20 | $Co_2(CO)_8$—$Ru_3(CO)_{12}$—$Fe(CO)_5$—DIPY[a,c] | " | 90[a] | 6.25 | P | 29.1 | 13.3 1.1 | 1.3 N.D. | <0.1 43.8 0.9 44.7 | 71 | 55 |
| 21 | $Co_2(CO)_8$—$Ru_3(CO)_{12}$—$Fe(CO)_5$—DIPY[a,d] | " | 90[a] | 5.50 | P | 28.5 | 8.0 0.3 | 1.9 N.D. | 28.8 0.2 29.0 | 64 | 36 |
| 22 | $Co_2(CO)_8$—Fe(phthalocyanine) | " | 90[a] | 1.25 | P | 27.5 | N.D. N.D. | 0.5 N.D. | N.D. N.D. <0.1 | N.D. | <0.1 |
| 23 | $Co_2(CO)_8$—$Fe(CO)_9$—DIPY[a] | " | 90[a] | 1.25 | P | 27.1 | 0.04 N.D. | 0.6 N.D. | <0.1 <0.1 N.D. <0.1 | N.D. | <0.1 |

[a] Run at 2000 psi (13,790 kPa) with ¼ (CO/H2) gas
[b] Co—Fe-ligand pretreated at 150° C.
[c] Co:Ru:Fe initial ratio 3:2:1
[d] Co:Ru:Fe initial ratio 2:1:1

We claim:

1. A catalyst composition comprising:
   a) A cobalt compound; and
   b) An iron component ligated with a ligand wherein the ligand is a 2,6-pyridyl-diimine.

2. The composition of claim 1 wherein the ligand is selected from the group consisting of 2,6-bis (N-phenyl, methylimido)pyridine and 2,6-bis[N-2,6-diisopropylphenyl) methylimido] pyridine.

3. A catalyst composition comprising:
   a) A cobalt compound; and
   b) An iron component ligated with a ligand, wherein the ligand is a tertiary diphosphine of the general formula:

RRP-Q-PR'R' wherein both groups R and/or R' form, with the phosphorous atom, a phosphacycloalkane of from 5 to 8 atoms, and Q is an organic bridging group of 2 to 4 atoms in length.

4. A catalyst composition comprising:
   a) A cobalt compound wherein the cobalt compound is a cobalt carbonyl; and
   b) An iron component optionally ligated with a ligand selected from the group consisting of N-heterocycle, phosphine, and porphorine moieties,
   wherein the cobalt compound is dicobalt octacarbonyl and the iron component is 2,3,7,8,12,13,17,18-octaethyl-21H, 23H-porphorine iron (III) acetate.

5. The composition of claim 4 wherein the molar ratio of Co:Fe:ligand is about 3:1:1.

* * * * *